United States Patent [19]
Koch et al.

[11] Patent Number: 4,479,888
[45] Date of Patent: Oct. 30, 1984

[54] DISPERSING ADDITIVES FOR LUBRICANTS, AND THE METHOD FOR THEIR PREPARATION

[75] Inventors: Paolo Koch, San Giuliano Milanese; Luciano Mattei; Giampaolo Gerbaz, both of Milan, all of Italy

[73] Assignee: Agip Petroli S.p.A., Rome, Italy

[21] Appl. No.: 156,427

[22] Filed: Jun. 4, 1980

[30] Foreign Application Priority Data

Aug. 10, 1979 [IT] Italy ................. 25049 A/79

[51] Int. Cl.$^3$ .............................................. B01F 17/16
[52] U.S. Cl. ................................... 252/357; 548/237; 548/239; 548/335; 252/51.5 A
[58] Field of Search ........................ 252/357, 51.5 A; 548/335, 237, 239

[56] References Cited

U.S. PATENT DOCUMENTS

| | | | |
|---|---|---|---|
| 3,389,145 | 6/1968 | Katz | 260/307 |
| 3,629,119 | 12/1971 | Weaver | 252/357 |
| 3,821,116 | 6/1974 | White et al. | 252/357 |
| 3,959,176 | 5/1976 | Mahn et al. | 252/356 |
| 4,000,150 | 12/1976 | Cambon et al. | 252/357 |
| 4,153,566 | 5/1979 | Ryer et al. | 252/51.5 A |
| 4,162,143 | 7/1979 | Yount | 252/356 |

*Primary Examiner*—Josephine Barr
*Attorney, Agent, or Firm*—Morgan, Finnegan, Pine, Foley & Lee

[57] ABSTRACT

Dispersing additives for lubricating fluids are disclosed, which contain the oxazoline function and are prepared by reacting amino alcohols with mono or bicarboxylic linear or branched chain aliphatic acids having from 2 to 51 carbon atoms. These additives are characterized by a very high dispersing power which makes them particularly suitable for engines used in stop-and-go service.

2 Claims, No Drawings

DISPERSING ADDITIVES FOR LUBRICANTS, AND THE METHOD FOR THEIR PREPARATION

This invention relates to dispersing additives for lubricants, and the method for their preparation.

More particularly, this invention relates to the preparation of a product soluble in mineral and synthetic oils which is used as a dispersing agent in lubricants which are particularly suitable for use in internal combustion engines.

When internal combustion engines are used for so-called "door to door" services, lubricants must be used having high dispersing power.

This requirement is a consequence of the accumulation of water and products which derive from partial combustion and lead to an abnormal formation of sludge which preferentially deposits on the engine fixed members and filter. These drawbacks are particularly felt under stop-go conditions, which are characteristic of public vehicles used for town transport, and of individual "door to door" services.

When an internal combustion engine is used under these conditions, the lubricant undergoes frequent heating and cooling cycles.

Sludge formation is drastically reduced by adding to the lubricant an oil-soluble compound of dispersing action, this compound having the specific purpose of keeping the sludge particles in solution and preventing their coagulation, otherwise they would separate out, so obstructing the filter and depositing on the fixed engine members.

A wide range of products is available for reducing sludge formation in internal combustion engine lubricants. These include polyamide polyisobutenylsuccinimides, Mannich bases derived from the condensation of polyisobutenylphenols with formaldehyde and polyamindes, polyisobutenylsuccinimides-succinesters derived from the condensation of polyisobutenylsuccinic anhydride with polyols and polyamines.

All these dispersing additives are organic compounds characterised by the presence in the same molecule of an oleophilic hydrocarbon chain and one or more polar and/or basic functions, the first having essentially the purpose of making the second soluble in oil.

Whereas the choice of the oleophilic chain is normally made only on the basis of its solubility in oil, economic convenience and availability, the choice of the polar and/or basic function is not as wide and casual as might appear at first sight.

This is because as this function can interact physically and chemically with other additives normally present in the lubricant (anti-oxidants, anti-corrosives, anti-rust agents, anti-wear agents, detergents), it can give rise to incompatibility.

In this respect, in many cases it has been found that the level of effectiveness of a certain additive is governed by the presence of certain polar groups present in the dispersing agent. It has now been found, and this constitutes a subject matter of the invention, that oil-soluble compounds containing the basic and polar function of oxazoline corresponding to the general formula:

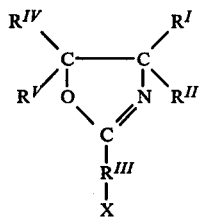

give exceptional dispersing properties to lubricants, and do not show incompatibility with other additives present.

Moreover, by suitably choosing the nature of the radicals $R^I$ to $R^V$ in the preceding formula, as will be specified and exemplified hereinafter, products are obtained which have dispersing action not only in mineral lubricant bases, but also in partially or totally synthetic bases, for which the additive problem always represented a problem of difficult or impossible solution prior to the present invention.

In the aforesaid general formula, $R^I$, $R^{II}$, $R^{IV}$ and $R^V$, which can be equal or different, are chosen from H, linear or branched alkyls with 1 to 10 carbon atoms, —$CH_2OH$ either free or esterified with a mono or bicarboxylic linear or branched chain aliphatic acid containing 2 to 51 carbon atoms, and/or with a succinic acid anhydride containing a hydrocarbon chain with 50 to 500 carbon atoms; however $R^{IV}$ and $R^V$ are preferably H.

$R^{III}$ is a linear or branched saturated or unsaturated hydrocarbon chain containing 1 to 500 carbon atoms, and X is hydrogen or a free or esterified —COOH group.

The products represented by general formula (I) are prepared, and this constitutes the second subject matter of the present invention, by reacting one or more amino alcohols of general formula:

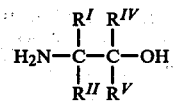

in which $R^I$, $R^{II}$, $R^{IV}$ and $R^V$ can be equal or different and be H, $CH_2OH$, linear or branched alkyls containing 1 to 10 carbon atoms, $R^{IV}$ and $R^V$ being preferably H, with a preferably equimolecular quantity of one or more mono or bicarboxylic linear or branched chain aliphatic acids containing 2 to 51 carbon atoms and exemplified by the formula $$X-R^{III}-COOH \qquad (III)$$

in which $R^{III}$ is a linear or branched saturated or unsaturated hydrocarbon chain containing 1 to 50 carbon atoms, and X can be H or COOH.

The bicarboxylic acid (III) can be replaced completely or partly by a succinic acid anhydride having a hydrocarbon chain containing a number of carbon atoms $C_n$ in which n is 50 to 500, and having the following structure:

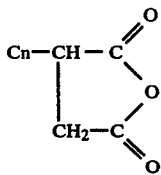

In this first stage, an acid group of (III) reacts with the amino alcohol (II), eliminating water:

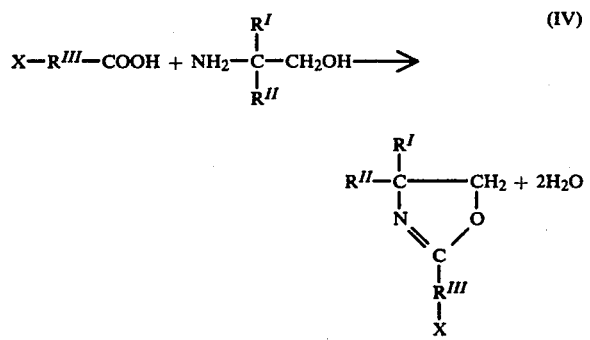

The nature of $R^I$, $R^{II}$, $R^{III}$ and X determine the presence of hydroxyl and/or free acid functions in (IV).

These products can be used as such, or, as has been found in many cases, can be further reacted with amino alcohols of general formula (II) or acids of general formula (III) to improve their performance and solubility in synthetic, mineral and synthetic-mineral lubricants.

The amino alcohol or acid used in this second stage can be either the same as or different from those used in the first stage.

The choice is made mainly on the basis of the type of lubricant base for which the product is intended.

By way of example, if the product of the first stage (IV) contains two free hydroxyl functions, and it is required to obtain a final product having dispersing properties in mineral bases, it can be advantageous to further react it with a mono or bicarboxylic acid (or a succinic acid anhydride as heretofore defined) containing an alkyl radical $R^{III}$ of high molecular weight, such that the final product contains long hydrocarbon chains which increase its affinity with mineral oils.

However, if the final product is intended for synthetic bases of ester type, it is advantageous to react the product of the first stage (IV) with mono or bicarboxylic acids containing shorter hydrocarbon chains, in order to increase its solubility in ester bases.

It is apparent that in both cases, these acid hydrocarbon chains become incorporated in the final product by the formation of ester functions with the free hydroxyls or carboxyl functions of the product (IV). It is also apparent that if in these cases bicarboxylic acids (or anhydrides) are used, products of polycondensation between the acid and the bifunctional alcohol (IV) are obtained.

For obvious practical reasons, it is desirable in many cases to obtain a final product which is soluble both in mineral oils and in synthetic oils. It has been found that this is possible by suitably proportioning the length of the hydrocarbon chain $R^{III}$. In this respect, continuing with the previous example, a product soluble in ester because it contains ester functions deriving from a short chain bicarboxylic acid can also be made soluble in mineral oils if it is made to derive from a product (IV) containing a radical $R^{III}$ of high molecular weight, and thus with strong affinity for mineral oils.

The reaction has always been described heretofore in terms of two separate stages, for obvious reasons of clarity of description. In many cases in fact it is effectively convenient to form the compound (IV) and then further react it, however this is not always necessary in that the amino alcohol can be made to react in a single stage with a suitable quantity of mono and bicarboxylic acids which are equal or different, thus simplifying the reaction and reducing reaction times.

These reactions are normally carried out in bulk at a temperature of 100° to 250° C., water removal being aided by a metered stream of inert gas. The progress of the reaction can be easily followed by the reduction in N.N. and by the increase in the absorption of the oxazoline group at 1660 cm$^{-1}$. It has been found preferable and convenient in many cases to dilute the reagents with mineral oil (normally to 50%) in order to obtain a more fluid final product, however the operational stages remain identical to those described.

The final products are characterised by IR (1660 cm$^{-1}$) and on the basis of the TBN. The oxazoline nitrogen, in contrast to the amide nitrogen, is in this respect strongly basic and can therefore be titrated with perchloric acid in an organic solvent.

Some examples are given hereinafter for the purpose of better illustrating the invention, which however is in no way limited by them.

EXAMPLE 1

1300 g of polyisobutene of $M_1$ 1290 are loaded into a four neck flask fitted with a stirrer, thermometer, bubbler and gas outlet. It is heated to 100° C., then maintaining energetic stirring $Cl_2$ is bubbled in, the rate being adjusted so that none escapes from the reactor. 73 g of $Cl_2$ are added in this manner, while maintaining the temperature at 100° C. At this point, the $Cl_2$ stream is interrupted, and is replaced by a $N_2$ stream, which is maintained until no further acid vapour leaves the reactor.

A sample is analysed for its chlorine content, which is found to be 2.7%. 1300 g of the previous chlorinated polyisobutylene and 115 g of maleic anhydride are placed in a three neck flask fitted with a stirrer, thermometer and condenser.

The mixture is heated to 180° C., and kept under energetic stirring at this temperature for 8 hours.

It is allowed to cool, the product diluted with 1 liter of n-hexane and filtered.

The filtrate is evaporated under vacuum while progressively heating to 100° C. to remove the last traces of solvent. The final product, polyisobutenylsuccinic anhydride (PIBSA), has a neutralisation number of 40 mg KOH/g.

140 g of the previously prepared PIBSA (0.1 moles) dissolved in 150 g of mineral oil are treated with 12.1 g of tris(hydroxymethyl)aminomethane (0.1 moles) in a three neck flask fitted with a stirrer, gas inlet and gas outlet. The temperature is gradually increased to 180° C. and kept at this level for 6 hours, a slight flow of inert gas aiding water removal.

The completion of the reaction is followed by I.R., and is indicated by the disappearance of the characteristic anhydride band at 1780 cm$^{-1}$, and by the increase in the characteristic oxazoline band at 1660 cm$^{-1}$. A final product is obtained having a N.N. of 2 mg KOH/g and a TBN of 12 mg KOH/g.

EXAMPLE 2

140 g of PIBSA prepared as in example 1 (0.1 moles) and 10.5 g of 2-amino-2-methyl-1,3-propanediol (0.1 moles) are dissolved in 150 g of mineral oil.

The temperature is raised to 180° C. while maintaining energetic stirring and a light flow of inert gas to aid water removal.

After 6 hours, the characteristic I.R. band of PIBSA at 1780 cm$^{-1}$ has disappeared. The final product has a TBN of 10 and a N.N. of 2.

EXAMPLE 3

140 g of PIBSA of example 1 (0.1 moles) and 8.9 g of 2-amino-2-methyl-1-propanol (0.1 moles) in 150 g of mineral oil are kept at 180° C. under energetic stirring and under an inert gas stream for 6 hours. The PIBSA band at 1780 cm$^{-1}$ is absent in the final product, which has a TBN of 8 and a N.N. of 4.

EXAMPLE 4

140 g of PIBSA of example 1 (0.1 moles) and 13.3 g of 2-amino-2-methyl-1-propanol (0.15 moles) in 150 g of mineral oil are reacted as in the preceding example.

The final product has a TBN of 8.5 and a N.N. of 3.5.

EXAMPLE 5

140 g of PIBSA of example 1 (0.1 moles) and 17.8 g of 2-amino-2-methyl-1-propanol (0.2 moles) in 150 g of mineral oil are reacted as in example 3.

The final product has a TBN of 8.5 and a N.N. of 3.

EXAMPLE 6

28.4 g of isostearic acid (0.1 moles) and 12.1 g of tris(hydroxymethyl)aminomethane (0.1 moles) are placed in a flask fitted with a stirrer, thermometer and gas inlet and outlet.

The mixture is heated for 3 hours at 180° C., and water removal from the reactor is aided by a light inert gas stream.

140 g of PIBSA (0.1 moles) prepared as in example 1 and dissolved in 180 g of mineral oil are then added.

The temperature is raised to 200° C. and the flow of inert gas maintained for a further 4 hours.

The I.R. anhydride band at 1780 cm$^{-1}$ is absent in the final product, which has a TBN of 15 and a N.N. of 0.8.

EXAMPLE 7

21 g of 2-amino-2-methyl-1,3-propanediol (0.2 moles) and 57 g of isostearic acid (0.2 moles) are placed in a flask fitted with a stirrer, thermometer and gas inlet and outlet. The mixture is heated for 3 hours at 180° C. during which a light stream of inert gas aids water removal from the reactor. 220 g of oil and 140 g of PIBSA (0.1 moles) prepared as in example 1 are then added. The mixture is heated under stirring to 200° C. for 4 hours while maintaining a flow of inert gas.

The final product has a TBN of 24 and a N.N. of 0.4, and the anhydride band at 1780 cm$^{-1}$ is completely absent.

EXAMPLE 8

12.1 g of tris(hydroxymethyl)aminomethane (0.1 moles) and 16 g of pelargonic acid (0.1 moles) are placed in a three neck flask fitted with a stirrer, gas inlet and gas outlet.

The mixture is heated for 3 hours at 180° C., water removal from the reactor being facilitated by a stream of inert gas. 140 g of PIBSA (0.1 moles) prepared as in example 1 dissolved in 170 g of mineral oil are then added. The mixture is heated under stirring for more than 4 hours at 200° C. The final product has a TBN of 21 and a N.N. of 1.4, the anhydride band at 1780 cm$^{-1}$ being absent.

EXAMPLE 9

12.1 g of tris(hydroxymethyl)aminomethane (0.1 moles) and 28.5 g of isostearic acid (0.1 moles) are placed in a three neck flask fitted with a stirrer, gas inlet and gas outlet. The mixture is heated to 180° C. for 3 hours, after which 57 g of isostearic acid (0.2 moles) are added. The mixture is heated under stirring for 4 hours, water removal from the reactor being facilitated by a stream of inert gas. The final product is diluted with 100 g of mineral oil and has a TBN of 32 and a N.N. of 2.

EXAMPLE 10

21 g of 2-amino-2-methyl-1,3-propanediol (0.2 moles) and 31.6 g of pelargonic acid (0.2 moles) are placed in a flask fitted with a stirrer, gas inlet and gas outlet. The mixture is heated to 180° C. for 3 hours, facilitating the removal of water from the reactor by a stream of inert gas. 140 g of PIBSA (0.1 moles) prepared as in example 1 and dissolved in 190 g of mineral oil are then added.

The mixture is heated to 200° C. for 4 hours while maintaining the inert gas flow into the reactor. The final product has a TBN of 19 and a N.N. of 2, the anhydride band at 1780 cm$^{-1}$ being absent.

EXAMPLE 11

65 g of enanthic acid (0.5 moles) and 60.5 g of tris(hydroxymethyl)aminomethane (0.5 moles) are placed in a flask fitted with a stirrer, gas inlet and gas outlet. The mixture is heated to 180° C. for 3 hours while maintaining a flow of inert gas to facilitate water removal from the reactor. 210 g of Empol 1010 ($C_{36}$ aliphatic carboxylic acid) equal to 0.373 moles are then added, and heating is continued at 200° C. for more than 4 hours. The IR spectrum for the product obtained shows the free acid carboxylic band at 1700 cm$^{-1}$ to be absent, while the hydroxyl band at 3300–3500 cm$^{-1}$ is present.

33 g of enanthic acid (0.254 moles) are then added, and heating is continued at 200°–220° C. for more than 6 hours. The hydroxyl band at 3300–3500 cm$^{-1}$ is absent in the final product, which has a N.N. of 1.5 and a TBN of 71.9.

The product obtained is miscible in all proportions with synthetic lubricating oils of ester type. It is not soluble in mineral oil.

EXAMPLE 12

85 g of isostearic acid (0.3 moles) and 36 g of tris(hydroxymethyl)aminomethane (0.3 moles) are placed in a three neck flask fitted with a stirrer, gas inlet and gas outlet. The mixture is heated to 180° C. for 3 hours while maintaining a flow of inert gas to facilitate water removal from the reactor. 126 g of Empol 1010 (0.224 moles) are then added, and heating is continued at 200° C. for more than 4 hours. When analysed by IR the product obtained shows no bands attributable to free carboxylic functions at 1700 cm$^{-1}$.

However, under IR the product shows the characteristic absorption of hydroxyl bands at 3300–3500 cm$^{-1}$.

43 g of isostearic acid (0.152 moles) are then added, and heating is continued at 200°–220° C. for more than 6 hours while maintaining the flow of inert gas.

Hydroxyl bands at 3300–3500 cm$^{-1}$ are absent in the final product, which has a N.N. of 0.8 and a TBN of 60.

The product obtained is miscible both with synthetic oils of ester type and with mineral oils.

Application tests

The dispersants of the examples were tested on a Fiat 600 D engine in accordance with the CEC-L-04-A-70 procedure.

This method is currently used for evaluating the anti-sludge and dispersing properties of lubricants for petrol engines working under low temperature conditions, these being conditions typical of town travel.

The method is based essentially on evaluating the sludge accumulation in the centrifugal filter and on the fixed members during the test.

The dispersants according to the present invention were examined at a concentration of 1% in a mineral base known as "Solvent Neutral 450 SUS at 100° F." and in a synthetic base consisting of a monoesterified trimethylolpropane adipate.

The table hereinafter gives the results obtained, and for comparison purposes also gives the results obtained for the lubricant base without additive and also, in the case of the synthetic base, with a commercial dispersing additive derived from polyisobutene.

| Oil type | Additive 1% | Engine sludge Hours of test | Grams in centrif. filter |
|---|---|---|---|
| Mineral | — | 132 | 82 |
| Mineral | Ex. 1 | 270 | 20 |
| Mineral | Ex. 6 | 270 | 51.8 |

| Oil type | Additive 1% | Engine sludge -continued Hours of test | Grams in centrif. filter |
|---|---|---|---|
| Mineral | Ex. 7 | 270 | 42 |
| Ester | — | 216 | 23.6 |
| Ester | Commercial | 54 | 26 |
| Ester | Ex. 11 | 216 | 19.2 |

We claim:

1. A process for preparing dispersing additives for mineral or synthetic lubricants, comprising the steps of:
   (a) reacting one or more amino alcohols of the formula:

$$H_2N-\underset{\underset{R^{II}}{|}}{\overset{\overset{R^{I}}{|}}{C}}-CH_2-OH$$

wherein $R^I$ is —CH$_2$OH and $R^{II}$ is hydrogen, a branched or unbranched alkyl having from 1 to 10 carbon atoms, or is equal to $R^I$, with an equimolar amount of a saturated monocarboxylic acid of the formula:

$$R^{III}COOH$$

wherein $R^{III}$ is a branched or unbranched alkyl having from 1 to 49 carbon atoms; and
   (b) reacting the product of step (a) with a polyisobutenylsuccinic anhydride carrying a hydrocarbon chain having from 50 to 500 carbon atoms, or with a saturated monocarboxylic acid of the formula:

$$R^{III}COOH$$

wherein $R^{III}$ is as hereinbefore defined.

2. The process of claim 1, wherein the first step is carried out at a temperature of about 180° C. and the second step at a temperature of about 200° C.

* * * * *